(12) United States Patent
Baru et al.

(10) Patent No.: US 9,681,843 B2
(45) Date of Patent: Jun. 20, 2017

(54) NERVE CUFF STIMULATION ELECTRODE, CONTROL DEVICE FOR A VAGUS NERVE STIMULATION SYSTEM, AND VAGUS NERVE STIMULATION SYSTEM

(71) Applicant: BIOTRONIK SE & Co. KG, Berlin (DE)

(72) Inventors: Marcelo Baru, Tualatin, OR (US); Andrew B. Kibler, Lake Oswego, OR (US); Warren Dabney, Lake Oswego, OR (US); Jie Lian, Beaverton, OR (US); Christopher Moulder, Portland, OR (US); Dirk Muessig, West Linn, OR (US)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 14/745,776

(22) Filed: Jun. 22, 2015

(65) Prior Publication Data

US 2015/0374296 A1    Dec. 31, 2015

Related U.S. Application Data

(60) Provisional application No. 62/017,282, filed on Jun. 26, 2014.

(51) Int. Cl.
| | | |
|---|---|---|
| *A61B 5/00* | (2006.01) |
| *A61B 5/11* | (2006.01) |
| *A61N 1/05* | (2006.01) |
| *A61N 1/28* | (2006.01) |
| *A61N 1/36* | (2006.01) |
| *A61B 5/0205* | (2006.01) |
| *A61B 5/0215* | (2006.01) |
| *A61B 5/021* | (2006.01) |

(52) U.S. Cl.
CPC .......... *A61B 5/6877* (2013.01); *A61B 5/0205* (2013.01); *A61B 5/0215* (2013.01); *A61B 5/1116* (2013.01); *A61N 1/0556* (2013.01); *A61N 1/28* (2013.01); *A61N 1/36053* (2013.01); *A61B 5/002* (2013.01); *A61B 5/02125* (2013.01)

(58) Field of Classification Search
CPC .................................................. A61B 5/6877
See application file for complete search history.

(56) References Cited

U.S. PATENT DOCUMENTS

| | | |
|---|---|---|
| 8,401,640 B2 | 3/2013 | Zhao et al. |
| 8,473,068 B2 | 6/2013 | Farazi |
| 2013/0184773 A1 | 7/2013 | Libbus et al. |

(Continued)

*Primary Examiner* — Eric D. Bertram
(74) *Attorney, Agent, or Firm* — Muncy, Geissler, Olds & Lowe, P.C.

(57) ABSTRACT

A nerve cuff stimulation electrode for cervical VNS is provided and configured to be arranged so as to at least partially surround or enclose one of the vagus nerves. The cuff stimulation electrode has at least two contacts configured to deliver electric stimulation pulses to a vagus nerve. The cuff stimulation electrode further has or may be attached or connected to a tilt sensor, a kinematic sensor, and/or a pulsation sensor configured to generate a signal representative of arterial and venous pressures. The implantable tilt sensor is configured to output a posture signal indicating a patient's posture, thus allowing discrimination between supine and semi-recumbent or erect postures.

15 Claims, 5 Drawing Sheets (56) References Cited

U.S. PATENT DOCUMENTS

2013/0231726 A1* 9/2013 Johnson ............... A61N 1/0556
                                                     607/118
2014/0188202 A1* 7/2014 Zarembo .............. A61N 1/0556
                                                     607/118

* cited by examiner

NERVE CUFF STIMULATION ELECTRODE, CONTROL DEVICE FOR A VAGUS NERVE STIMULATION SYSTEM, AND VAGUS NERVE STIMULATION SYSTEM

This nonprovisional application claims priority to U.S. Provisional Application No. 62/017,282, which was filed on Jun. 26, 2014, and which is herein incorporated by reference.

BACKGROUND OF THE INVENTION

Field of the Invention

The present invention relates to a nerve cuff stimulation electrode, a control device for a Vagus Nerve Stimulation (VNS) system, and a VNS system.

Description of the Background Art

Vagus Nerve Stimulation (VNS) systems and methods are inter alia disclosed in U.S. Pat. No. 8,401,640, US 2013/0184773 and U.S. Pat. No. 8,473,068.

Cervical VNS may be used for the treatment of Congestive Heart Failure (CHF).

Conventional chronic implantable apparatuses for VNS for the treatment of CHF generally involve implanting a cervical nerve cuff electrode for stimulation that connects via wires to an Implantable Pulse Generator (IPG) in a patient's chest. A standard pacemaker sensing lead in the ventricle has been disclosed for the purpose of synchronous delivery of VNS pulses in the cardiac refractory period. This sensing lead allows for certain cardiac timing monitoring. However, there is a need for an improved VNS system.

Chronic implantable VNS for CHF apparatuses in the prior art generally lack monitoring capabilities for disease progression, or these are limited to cardiac timing and transthoracic impedance measurements which require leads in the heart. Since the targeted CHF patient population may require implantation of an implantable cardioverter/defibrillator to prevent sudden cardiac death or another cardiac rhythm management device, it is preferred to avoid adding leads in the heart for the purpose of delivering VNS therapy. Apparatuses in the prior art lack, in particular, the capability of measuring arterial or venous pressure waveforms, which are critical parameters in the assessment of complications related to CHF. Patient sleeping angles, as well as OSA-related parameters, can also give extra diagnostics information in this patient population. VNS for CHF apparatuses in the prior art lack these measurement capabilities as well.

Prior art apparatuses also suffer from limited lifetime, since they are powered from a primary battery, which requires a revision surgery to replace the IPG once its battery depletes. Rechargeable and inductively-powered IPGs, and wirelessly-powered nerve cuff electrodes with embedded electronics, have been proposed in prior art for other VNS therapies (e.g. epilepsy, obesity), but are not suitable for adaptation to VNS for CHF due to patience-compliance issues. A VNS for CHF apparatus cannot rely on the patient to provide power to deliver therapy.

SUMMARY OF THE INVENTION

It is therefore an object of the present invention to provide an improved VNS system that has a nerve cuff stimulation electrode for a cervical VNS configured to be arranged so as to at least partially surround or enclose one of the vagus nerves. The cuff stimulation electrode comprises a cuff and at least two contacts that are arranged on an inner cuff surface and that are configured to deliver electric stimulation to a vagus nerve. The cuff stimulation electrode may further comprise or may be attached or connected to a tilt sensor, a kinematic sensor, and/or a pulsation sensor, whose waveform depict volume representations of arterial and venous pressure pulses, which closely resemble pressure waveforms in appearance and timing. The implantable tilt sensor is configured to output a posture signal indicative of the patient's posture, thus allowing discrimination between supine and semi-recumbent or erect postures.

The term "nerve cuff stimulation electrode" can refer to, for example, a nerve cuff that has contacts for delivering electrical stimulation. A contact could also be referred to as "electrode pole". It is noted that the term "electrode" as used in some embodiments may refer to the cuff in its entirety and not to the electrode poles or contacts.

The tilt and kinematic sensors can be implemented via an accelerometer.

The cuff stimulation electrode may further comprise at least two additional contacts and associated connections, wherein the additional contacts can be arranged on the outer wall of the cuff stimulation electrode.

In an embodiment, the pulsation sensor can be based on electrical impedance plethsymography via the additional contacts.

Alternatively, the pulsation sensor may be based on strain gage.

Such a cuff stimulation electrode may be used in a VNS system and provides improved monitoring capabilities, in particular continuous monitoring of venous and arterial pressure waveforms and a patient's posture.

The tilt sensor may further incorporate a kinematic response for the extraction of heart rate and the diagnostics of Obstructive Sleep Apnea (OSA). When the cuff stimulation electrode is implanted so as to surround or enclose a vagus nerve, the cuff stimulation electrode is also arranged next to the Common Carotid Artery (CCA) and the Internal Jugular Vein (IJV) within the carotid sheath in the neck area. Thus, the pulsation sensor would pick up a signal that corresponds to the pressure waveforms in the IJV and the CCA. The signal provided by such a pulsation sensor may therefore be referred to as the "pressure signal," although it may only indirectly represents arterial and venous pressures in terms of shape and timing with respect to the cardiac cycle. Depending on the posture of the patient, this signal will either mainly depend on the IJV pressure waveform or the CCA one.

According to an exemplary embodiment of the invention, a control device is provided, that can be embedded in the cuff stimulation electrode assembly or connected to it, and can be configured to process posture and pressure waveform signals that are generated by the tilt and pulsation sensors, respectively, and that can evaluate the pressure waveforms based on the posture signal in order to allow discrimination of the IJV pressure waveform from the CCA pressure waveform.

The cuff stimulation electrode may comprise an interface to the control device for a data communication connection from and to the cuff stimulation electrode. The data communication connection may be a galvanic connection through the patient's body that comprises a data transceiver, and the additional contacts can be configured to provide data communication via modulation of an imposed alternating electric field.

In an embodiment, the tilt sensor is neither part of nor physically attached to the cuff stimulation electrode but connected to the control device instead as a part of the VNS system. In yet another embodiment, the tilt sensor may even be part of the control device as long as it can be implanted so that the tilt sensor orientation corresponds to the posture of a patient. In an embodiment, the combined tilt-kinematic sensor can be implemented using a triaxial accelerometer and the pulsation sensor can be implemented by electrical impedance plethsymography. In an embodiment, the pulsation sensor utilizes a displacement-sensitive measurement method instead, for example, a strain gage.

The control device can be configured to process posture signals and pressure signals that are generated by the tilt sensor and the pulsation sensor, respectively, the control device can also be configured to evaluate the pressure signals based on the posture signal, if the posture signal indicates a predetermined change of the orientation of the tilt sensor.

The control device may further be configured to extract a heart rate signal from the at least one sensor. The control device may alternatively or additionally be configured to determine congestive heart failure status from processing the sensor(s) signals.

In an embodiment, the control device can be configured to determine obstructive sleep apnea from processing the kinematic sensor signal.

The control device may be an implantable pulse generator with an internal power source.

The control device may further be configured to process posture signals and pulsation signals that are generated by the tilt sensor and the pulsation sensor, respectively, wherein the control device is further configured to evaluate the pulsation signals based on the posture signal, if the posture signal indicates a predetermined change of the orientation of the tilt sensor.

The control device may further have far-field electrogram recording capabilities. The control device may be configured to determine Congestive Heart Failure status from processing the sensor(s) signal(s) and the far-field electrogram recordings.

The control device may be further configured to determine Obstructive Sleep Apnea from processing the kinematic sensor signal.

The control device may be an implantable pulse generator.

The implantable pulse generator may further comprise wireless data communication with an external programmer or patient messenger.

In an embodiment, the cuff stimulation electrode including the tilt sensor and the pulsation sensor can be hermetically sealed for chronic implantation.

The nerve cuff stimulation electrode according to an embodiment of the invention is an implantable apparatus for cervical Vagus Nerve Stimulation (VNS) with the capability of recording Common Carotid Artery (CCA) and Internal Jugular Vein (IJV) pressure waveforms, among other key parameters applicable to the treatment of Congestive Heart Failure (CHF). This nerve cuff stimulation electrode can be implanted around one of the vagus nerves in the neck area, with internal stimulation contacts for delivering electrical stimulation to the nerve, a pulsation sensor, a triaxial accelerometer, and associated front-end electronic circuitry attached to or integrated into the stimulation electrode cuff's wall and all hermetically-sealed for chronic implantation. The front-end electronic circuitry may serve for stimulation and/or recording purposes. According to an embodiment, the nerve cuff stimulation electrode connects to a battery-operated Implantable Pulse Generator (IPG) in the patient's chest, which controls stimulation delivery, powers the cuff stimulation electrode electronic components, and receives pressure and acceleration signals for further processing.

The nerve cuff stimulation electrode can be implanted such that the pulsation and accelerometer sensors face the CCA/IJV outer walls. The accelerometer allows determining Obstructive Sleep Apnea (OSA)-related parameters, patient sleeping angles and heart rate, which can also be extracted from the CCA pressure waveform timing. It can also be used for arterial acceleration plethysmography, which highly correlates to systolic blood pressure.

The IPG is capable of performing intrathoracic far-field Electrogram (EGM) recording and processing for arrhythmia monitoring. The IPG has the possibility of communicating, via a MICS-band link or equivalent, to an external Programmer or bedside Patient Messenger connected to a Home Monitoring/Remote Programming Center.

In an embodiment, the apparatus incorporates the control device and it is powered by reliable body energy harvesting for continuous and autonomous operation, e.g. by a Thermoelectric Generator (TEG) implanted around the External Jugular Vein (EJV) and wired to the control device. The temperature difference between the EJV and the surrounding subcutaneous tissue below the skin provides enough of a temperature gradient to power the apparatus in the present application. The TEG can be held in place by a Ni-based vein cuff for external banding around the EJV.

In an embodiment, the apparatus communicates, via modulation of an imposed alternating electric field (Passive Z-COMM), with an external skin Patch connectable to a Programmer or to another implantable device, hence being suitable for integration in a Home Monitoring/Remote Programming regime, which is an important feature in the integral medical treatment of CHF patients. In an embodiment, the extra contacts on the nerve cuff stimulation electrode outer wall required for Passive Z-COMM can be multiplexed to perform impedance plethysmography for arterial blood flow assessment.

The nerve cuff stimulation electrode, the control device and the Vagus Nerve Stimulation (VNS) system comprising both, the nerve cuff stimulation electrode and the control device according to an embodiment of the invention, each advance the state-of-the-art in cervical VNS for CHF treatment by providing a system for continuous monitoring of venous and arterial pressures, cardiac timing for arrhythmia detection, in particular patient sleeping angles and parameters relevant to the diagnostics of OSA, without requiring endocardial leads.

Each vagus nerve is situated posteriorly between the Common Carotid Artery (CCA) and the Internal Jugular Vein (IJV) in the carotid sheath, a fibrous connective tissue that surrounds the vascular compartment of the neck. The nerve cuff stimulation electrode of the present invention takes advantage of this proximity and integrates a pulsation sensor (and associated front-end electronic circuitry) on its outer wall to indirectly measure the combined pressure waveforms of both vessels. Such combined pressure waveform can be further decomposed in the individual CCA and IJV pressure waveforms, based on the patient posture determined by, for example, the triaxial accelerometer. In the supine position, the IJV is partially distended and its higher compliance, with respect to the CCA, allows recording of a waveform that reflects the IJV pressure. On the other hand, in semi-recumbent and erect postures, the IJV vein normally collapses to a slit-like passage leaving only the CCA volume pulsations. Because the spectral content of respiratory waveforms and vascular waveforms overlap, a band-pass filter (that can be part of the cuff stimulation electrode's front-end circuitry or part of the control device) may allow eliminating the distortion caused by the former.

Present miniaturization technologies, and the length of the cuff stimulation electrode, allow integrating other electronics on the same electrode assembly. An embedded triaxial accelerometer (and associated front-end electronic circuitry) permits diagnosing Obstructive Sleep Apnea (OSA), and the static acceleration component permits monitoring sleeping angles. These two parameters are of particular interest, as patients with Congestive Heart Failure (CHF) generally suffer from sleep apnea, and they tend to sleep in a sitting position due to breathing difficulties. Statistics on the sleeping angle, for example, may be utilized to analyze improvements or worsening of a patient's condition. The same accelerometer may be used for acceleration plethysmography which allows an indirect measurement of the systolic blood pressure. Alternatively, the accelerometer is located within the IPG.

Electrical impedance plethysmography of the artery is also possible, with a minimum of two electrode contacts on the nerve cuff stimulation electrode's outer wall and the same stimulating electronic circuitry, which allows artery blood flow assessment. These two electrode contacts may be the same as the ones utilized for Passive Z-COMM communication. They may also be arranged to provide enough of a vector to extract a heart rate.

Although the heart rate can be extracted from the accelerometer or CCA pressure waveform, an intrathoracic far-field Electrogram (EGM) can be recorded between the IPG can (that is the IPG housing) and one of the nerve cuff stimulation electrode contacts or other dedicated electrode contacts to provide more meaningful cardiac timing information for arrhythmia detection purposes. All the available diagnostics, combined with wireless communication capability to a bedside Patient Messenger (an external device that can communicate with the implantable IPG), make the system of the present invention suitable for integration into a Home Monitoring/Remote Programming therapy regime. The same wireless link can be used for IPG programmability via an external Programmer.

With respect to powering the nerve cuff stimulation electrode by way of energy harvesting, the following has been observed. Given the location of the External Jugular Vein (EJV), the temperature difference with its surrounding tissue beneath the skin, and the very low power required for the nerve cuff stimulation electrode of the present application, the apparatus is powered by a TEG module (Seebeck effect) placed around the EJV using a Ni-based vein cuff for external banding. Implantation of this TEG module avoids long wire tunneling to a control device in the chest area, as it is located in the same neck area as the nerve cuff stimulation electrode. The vein cuff should provide enough support for connective tissue to grow and keep the TEG module in place. Such power supply of the nerve cuff stimulation electrode by way of energy harvesting can be implemented independently from other features of the nerve cuff stimulation electrode.

In an embodiment, the apparatus of the present invention can have two electrode contacts on its outer wall for galvanic intrabody data communication with an external skin Patch connectable to a Programmer, an implantable heart monitor or another implantable device via modulation of an imposed alternating electric field. Either the heart monitor or the skin Patch (which can operate autonomously) may communicate via a MICS-band link (or equivalent) to a bedside Patient Messenger connected to a Home Monitoring/Remote Programming Center.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION OF THE INVENTION

Figure 1:
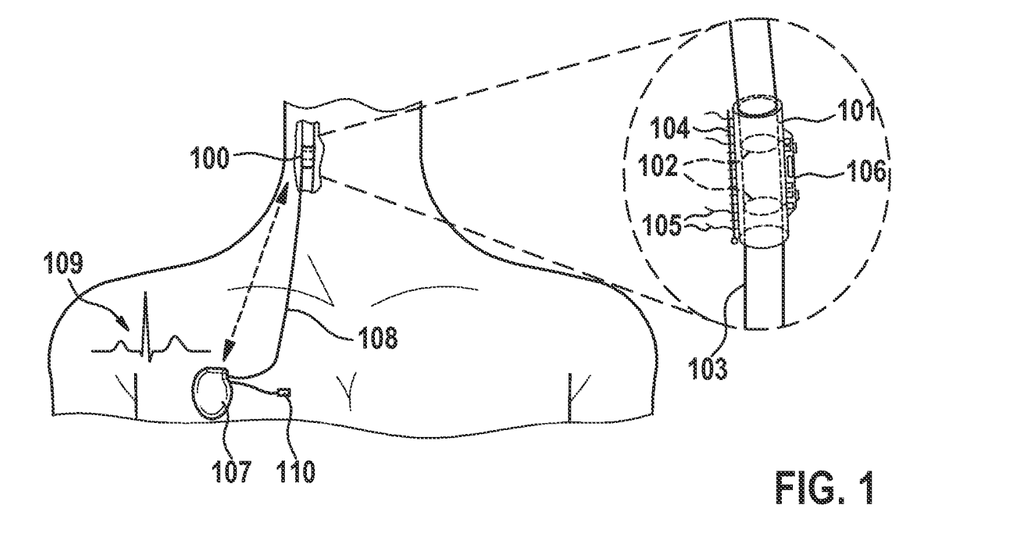
FIG. 1 is an illustration of an implanted cuff stimulation electrode and control device according to an exemplary embodiment of the invention.

According to an exemplary embodiment of the invention as shown in FIG. 1, a nerve cuff stimulation electrode 100 is constructed, using a silicone rubber tube 101, with at least two exposed Pt/Ir (or equivalent material) ring contacts 102 in its interior wall in contact with the vagus nerve 103 surface, and a closing structure 104. The cuff stimulation electrode 100 can be self-coiling, or it may include other closing mechanisms, such as a piano hinge with a nylon suture. Biocompatible strings 105 are built on the cuff stimulation electrode 100 outer wall to open it for easy implantation around the nerve 103. Electronic circuitry 106, which may include a pulsation sensor, a triaxial accelerometer, and associated front-end electronic circuitry, is built on the cuff stimulation electrode 100 outer wall and/or associated assembly structures.

In an exemplary embodiment, the ring contacts 102 are replaced by multiple contacts around the nerve 103. Local bipolar stimulation between any two of these contacts may increase effectiveness and selectivity for cardiovascular effects.

The nerve cuff stimulation electrode 100 is connectable to an Implantable Pulse Generator (IPG) 107 located in the patient's chest area via a subcutaneously implanted wire 108. Such wire 108 provides electrical connection to the contacts 102, powers the electronic module 106 built on the cuff stimulation electrode 100, and receives pre-processed pressure and acceleration signals from the vicinity of the cuff stimulation electrode 100. Electronic circuitry in the IPG 107 can drive the ring contacts 102 for delivering low-level electrical stimulation pulses to the nerve 103, i.e. a stimulation level that may not cause a heart rate drop or any other noticeable effect in the patient. Sub-threshold pulses can also be delivered through the ring contacts 102 for impedance measurement to assess potential nerve 103 damage, connective tissue growth, or closing structure 104 failure. The IPG 107 also has the capabilities of recording intrathoracic far-field EGMs 109 between its can and a contact 102, or alternatively using a separate lead with contact(s) 110 closer to the heart. Thus, the IPG 107 acts as a control device for the cuff stimulation electrode 100. It should be noted that the control device may also be another device different from an IPG.

Figure 2:
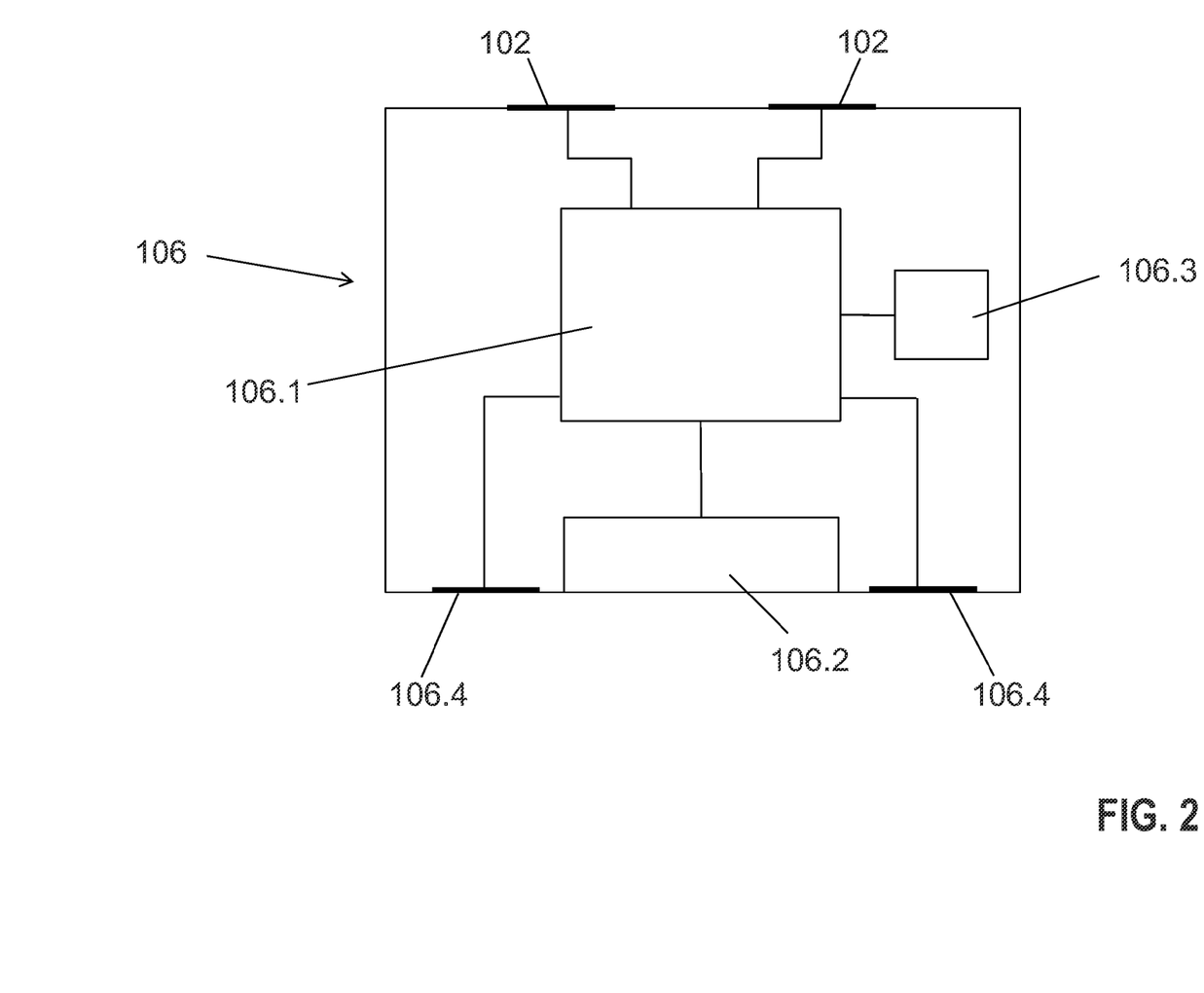
FIG. 2 is a schematic block diagram of the main electronic components (front-end) of the cuff stimulation electrode.

FIG. 2 is a schematic block diagram showing the main electronic components of the nerve cuff stimulation electrode 100. These may include a pulsation sensor 106.2, which utilizes a displacement-sensitive measurement method (e.g. a strain gage), and a triaxial accelerometer 106.3, both connected to the front-end electronic circuitry 106.1. Such circuitry 106.1 may be connected to stimulation contacts 102 and/or to communication contacts 106.4. These contacts 106.4 may serve for galvanic intrabody data communication via modulation of an imposed alternating electric field on the body. They can be part of a data communication interface of the IPG 107. For the purpose of data communication, the IPG 107 may comprise a data transceiver connected to communication contacts 106.4. In an embodiment, the pulsation sensor is based on electrical impedance plethsymography re-utilizing these contacts 106.4 (multiplexed with communication) and the IPG 107 circuitry utilized for nerve 103 impedance measurements.

Figure 3:
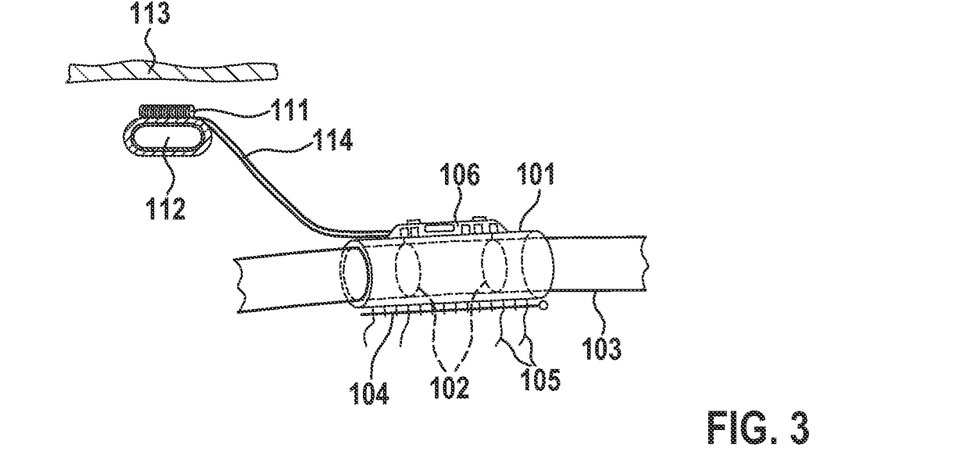
FIG. 3 is an illustration of a cuff stimulation electrode that incorporates the control device and is connected to an implanted Thermoelectric Generator (TEG)

In an embodiment, the control device is integrated with the electronic circuitry 106 and powered by a Thermoelectric Generator (TEG) module 111 implanted around the External Jugular Vein (EJV) 112 using a Ni-based vein cuff, with the TEG's hot plate in thermal contact with the EJV 112 outer wall and the cold plate facing the surrounding tissue beneath the skin 113, as shown in FIG. 3. A temperature difference of 2 K can be expected between the two plates of the TEG module 111, and such temperature difference can be converted (by Seebeck effect) into electrical energy for powering the embedded electronic circuitry 106. Typically 1.0 V at 5.0 μA or 5.0 μW can be harvested with this TEG. This is enough power for the particular application given that VNS for CHF is duty cycled with a few pulses delivered every few seconds or cardiac cycles. A typical stimulation pulse may have a rectangular pulse of 1.0 mA with a 200 μs width which requires negligible charge consumption compared with the background power consumption required for operation. Most of the power consumption in the present application is required for signal processing from the mentioned sensors.

The circuitry 106 in this case includes the necessary low-power management circuitry for power regulation and continuous operation. Power supply from the TEG module 111 to the control device and electronic circuitry 106 is provided by the power supply wire 114.

Figure 4:
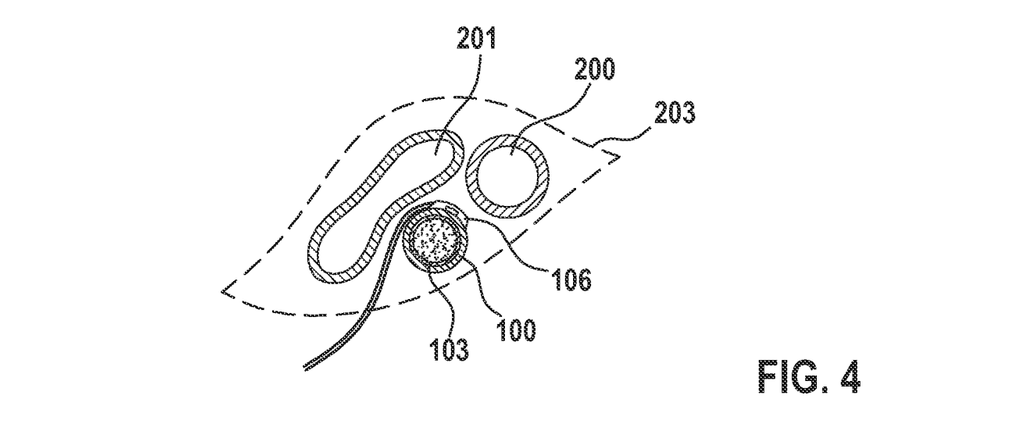
FIG. 4 is a cross-sectional view of the vagus nerve, the Common Carotid Artery (CCA) and the Internal Jugular Vein (IJV) within the carotid sheath in the neck area.

FIG. 4 sketches a cross-sectional view of the vagus nerve 103, the Common Carotid Artery (CCA) 200 and the Internal Jugular Vein (IJV) 201 within the carotid sheath 203 in the neck area. As can be seen, the nerve cuff electrode 100 is implanted so its built-in electronic circuitry 106 faces the CCA 200 and IJV 201 for pressure waveform recording. In an embodiment, the nerve cuff electrode 100 may partially or fully wrap at least one of the CCA 200 and IJV 201 for improved pressure waveform recording.

Figure 5:
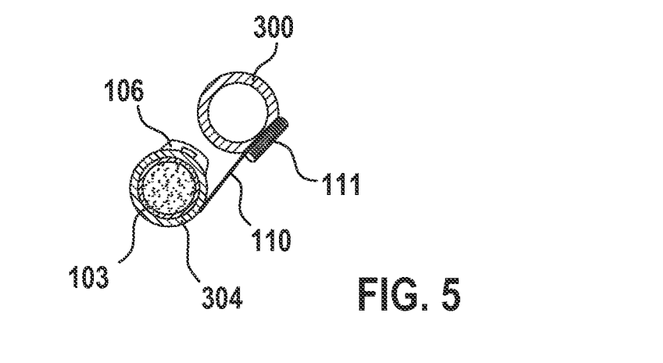
FIG. 5 is an illustration of an exemplary embodiment, wherein the TEG module is placed with its hot plate adjacent to the CCA and its cold plate facing surrounding tissue away from the IJV.

As can be taken from FIG. 5, the TEG module 111 is instead placed with its hot plate adjacent to the CCA 300 and its cold plate facing surrounding tissue away from the blood vessel, for instance the IJV. The TEG module 111 anchoring may be part of the cuff 304, wrapping both the vagus nerve 103 and the CCA 300. As can be seen in FIG. 5, the cuff 304 is implanted so its embedded electronic circuitry 106 faces the CCA 300.

As pointed out above, the signal provided by the pulsation sensor 106.2 is representative of arterial and venous pressures in terms of shape and timing with respect to the cardiac cycle and thus can be considered an indirect pressure signal.

Figure 6:
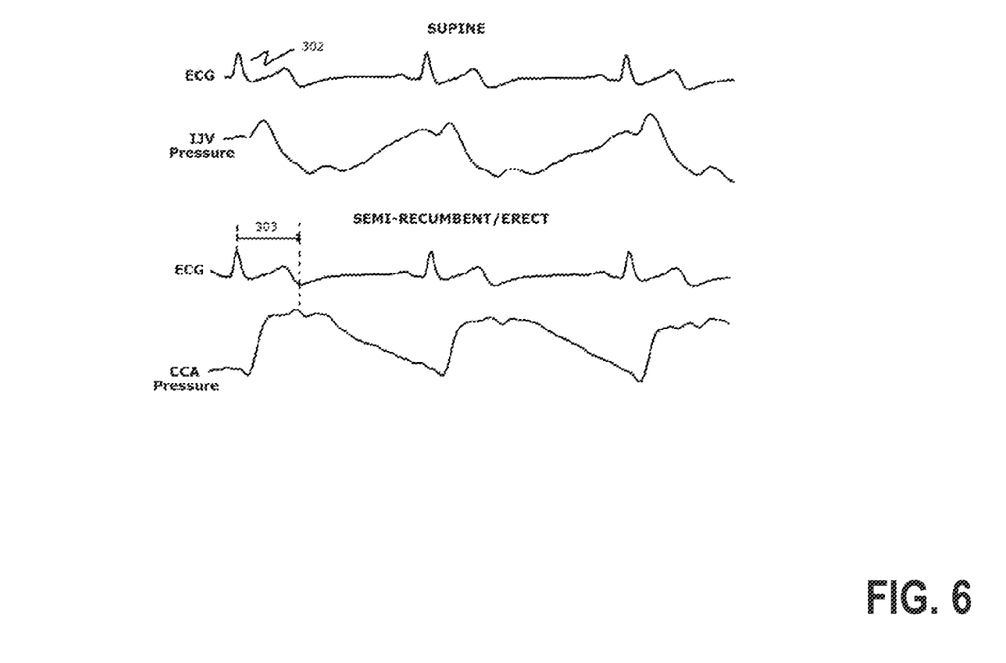
FIG. 6: is an illustration of an IJV and a CCA pressure waveform.

The CCA 200 and IJV 201 pressure waveforms provide relevant information about the patient's heart condition and hence are very useful for the monitoring of CHF status. As shown in FIG. 6, the IJV pressure waveform can be differentiated from the CCA pressure waveform by recording when the triaxial accelerometer indicates a supine and a semi-recumbent or erect position, respectively. The sampled pressure waveform is band-pass filtered to eliminate or minimize respiratory components. In an embodiment, the lower limit of the digital linear phase filter is set to a frequency above the fundamental respiratory rate and below the fundamental heart rate. The upper limit, on the other hand, can be set to reduce electrical noise from the mains. The front-end electronic circuitry 106.1 is configured to filter the pressure signal with a lower cutoff frequency between 0.75 Hz-1.75 Hz and an upper cutoff frequency between 20 Hz-30 Hz. The pressure signal either represents the IJV or CCA pressure based on the patient's position. An exemplary sampling rate can be 200 Hz.

The accelerometer signal provided by the triaxial accelerometer 106.3 is pre-processed by the front-end electronic circuitry 106.1 to determine heart and respiratory signals as follows:

Breathing signal band-pass: 0.10 Hz-0.50 Hz.
Heart rate signal band-pass: 0.50 Hz-3.50 Hz.
Snoring signal band-pass: 3.5 Hz-100.0 Hz.

Also in an embodiment, morphological filters are implemented in the IPG 107 embedded electronic circuitry to track changes in the IJV and CCA pressure waveforms. The parameters of these filters may be adjusted following implantation. Deviations from the original waveforms with time will indicate heart complications that may occur with the progression of the patient's condition. In addition, changes in the Pulse Transit Time (PTT) 303, i.e. the delay between the R-wave detection and the peak of the CCA pressure waveform, can be used to determine arterial stiffness and to perform monitoring of arterial blood pressure. PTT trending analysis can be used to assess disease progression.

The system of the present invention has the signal processing capabilities to identify changes that may occur in the CCA and IJV pressure waveforms and alerting, for example, a Home Monitoring Center via a bedside Patient Messenger.

In an embodiment, the system of the present invention has the signal processing capabilities to identify changes that may occur in the CCA and IJV pressure waveforms and alert, for example, a Home Monitoring Center accordingly either via a skin Patch when applied or by relaying the information to a heart monitor implanted device with wireless communication with the outside world.

As mentioned above, the triaxial accelerometer 106.3 signal can also be filtered in different ways to extract heart, breathing and snoring signals, which are key elements for the diagnosis of OSA. It can also be used to extract sleeping angle patterns. A decrease in the patient's sleeping angle will indicate an improvement of the patient's condition, as patients with CHF tend to sleep with several pillows due to breathing difficulties associated with the disease. Furthermore, the accelerometer can be used to determine the Reflected Wave Transit Time (RWTT) of the CCA pulse wave, which is the temporal difference between the incident and reflected wave at the same position. It has been shown in vivo that the RWTT has high correlation with systolic blood pressure, and hence it can be used as an estimator.

Figure 7:
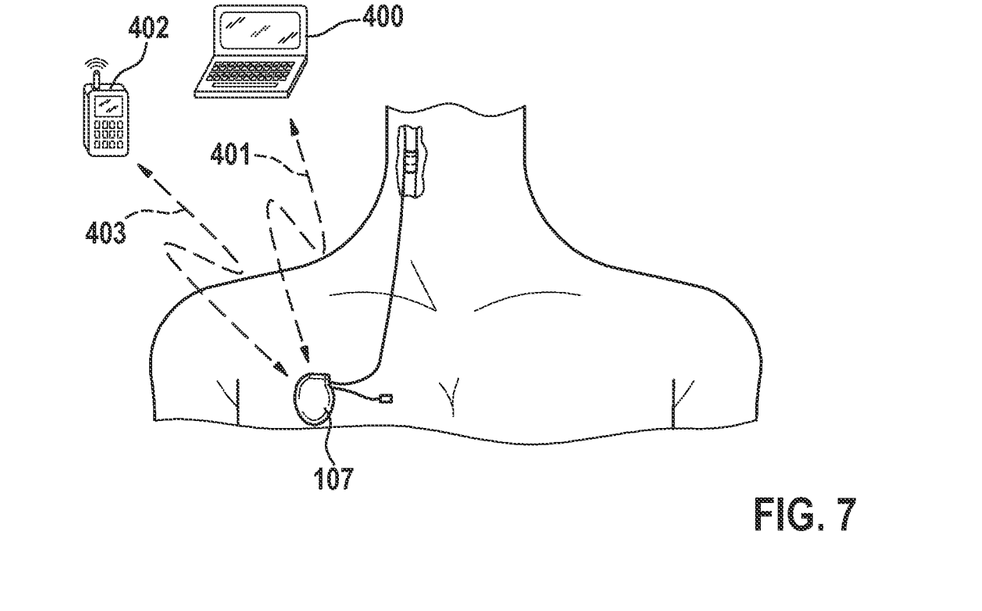
FIG. 7: illustrates a communication scheme with an implantable nerve stimulation system.

Going to FIG. 7, the IPG 107 can be wirelessly programmed by an external Programmer 400 via a MICS-band link 401 (or equivalent). The IPG 107 can also communicate with a bedside Patient Messenger 402 via a similar link 403. Arrhythmia detection, blood pressure waveform changes, and the other relevant diagnostic parameters described before can be transmitted to the bedside Patient Messenger 402 who can alert a Home Monitoring/Remote Programming Center, if medical attention is required.

Figure 8:
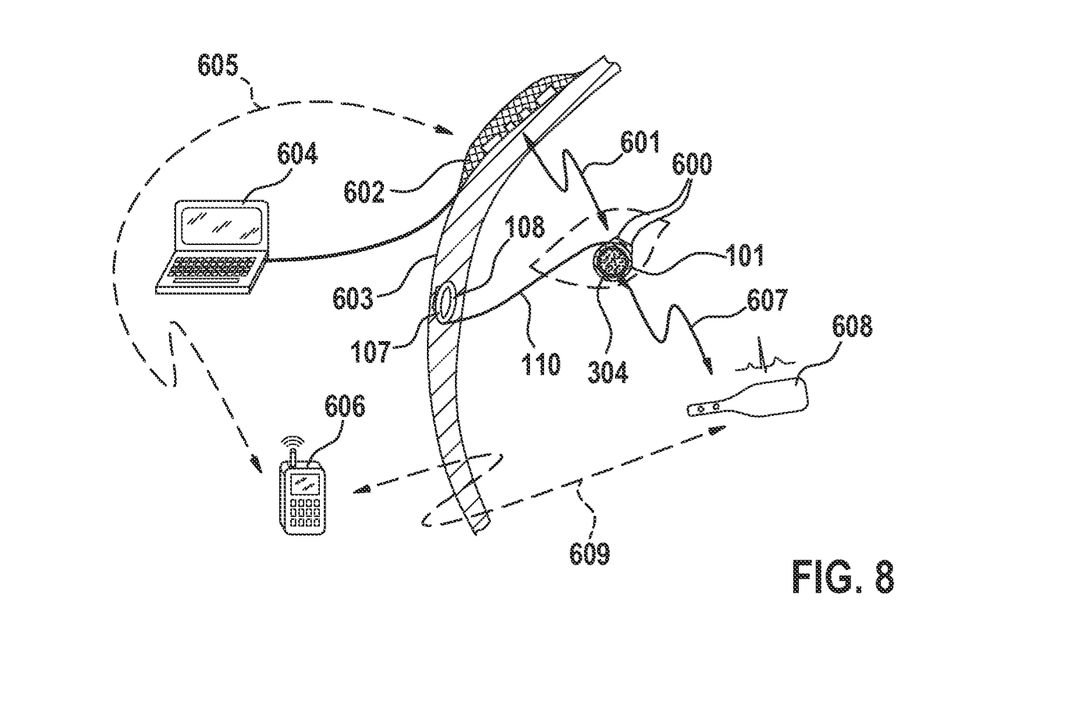
FIG. 8: illustrates a communication scheme with an implantable nerve stimulation system.

Referring to FIG. 8, the nerve stimulation electrode cuff 304 includes a minimum of two external contacts 600 placed longitudinally across its outer wall that can be used for galvanic communication 601 with an external skin Patch 602 applied on the patient's neck 603 or adjacent upper body location and wired to an external Programmer 604. The external skin Patch 602 can also be employed as an ambulatory monitor, if desired, with a low-power wireless link 605 to a bedside Patient Messenger 606 connected to, for example, a Home Monitoring/Remote Programming Center. The external contacts 600 can also be used for heart rate determination.

In an embodiment, the same communication contacts 600 of FIG. 8 for galvanic intrabody communication via modulation of an imposed alternating electric field can be multiplexed and utilized for impedance plethysmography that indirectly allows measuring the pulsatile blood flow through the CCA. The circuitry built-in for nerve impedance measurement can be used for this purpose.

The nerve cuff stimulation electrode 304 may also communicate via galvanic intrabody communication 607 with an implantable heart monitor 608 or another implantable device with the capability of MICS-communication 609 (or equivalent) with the bedside Patient Messenger 606.

Technical advantages of this invention include at least: a nerve cuff stimulation electrode with built-in electronic circuitry that includes a pulsation sensor (e.g. electrical impedance plethsymography or strain gauge), a tilt-kinematic sensor (e.g. a triaxial accelerometer), and associated front-end electronic circuitry, implanted as a standard VNS cuff for CHF; a VNS for CHF system, capable of recording CCA and IJV pressure waveforms, critical parameters for CHF monitoring, in addition to other relevant parameters, such as heart rate, OSA-related, body posture, etc.; a VNS for CHF system, capable of recording intrathoracic far-field EGMs for arrhythmia detection in particular; and/or a VNS for CHF system, suitable for integration into a Home Monitoring/Remote Programming regime or another monitoring device.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A vagus nerve stimulation system comprising:
a control device; and
a cuff stimulation electrode, the cuff stimulation electrode comprising:
an inner cuff surface that faces a nerve;
at least two contacts arranged on the inner cuff surface for delivering electrical stimulation; and
at least one sensor attached to an outer wall of the cuff stimulation electrode, the at least one sensor including a tilt sensor, a kinematic sensor, and/or a pulsation sensor,
wherein the at least one sensor is configured to generate a signal representative of physiological parameters, and
wherein the control device records far-field electrogram and wherein the control device determines Congestive Heart Failure status from processing the at least one sensor signal and the far-field electrogram recordings.

2. The cuff stimulation electrode according to claim 1, wherein the tilt and kinematic sensors are implemented using an accelerometer.

3. The cuff stimulation electrode according to claim 1, further comprising at least two additional contacts and associated connections, the additional contacts being attached to the outer wall of the cuff stimulation electrode.

4. The cuff stimulation electrode according to claim 3, wherein the pulsation sensor is based on electrical impedance plethsymography via the additional contacts.

5. The cuff stimulation electrode according to claim 3, further comprising an interface to a control device for a data communication connection from and to the cuff stimulation electrode.

6. The cuff stimulation electrode according to claim 5, wherein the data communication connection is a galvanic connection through a patient's body that comprises a data transceiver, and wherein the additional contacts provide data communication via modulation of an imposed alternating electric field.

7. The cuff stimulation electrode according to claim 3, wherein the at least one sensor and the at least two additional contacts are provided in a common housing attached to the outer wall.

8. The cuff stimulation electrode according to claim 1, wherein the pulsation sensor is a strain gage.

9. The cuff stimulation electrode according to claim 1, wherein the cuff stimulation electrode further comprises or is electrically connectable to a thermoelectric generator that is configured to be placed adjacent to a blood vessel.

10. The cuff stimulation electrode according to claim 1, wherein the control device of the cuff stimulation electrode processes posture signals and pressure signals that are generated by the tilt sensor and the pulsation sensor, respectively, and wherein the control device evaluates the pressure signals based on the posture signal, if the posture signal indicates a predetermined change of an orientation of the tilt sensor.

11. The A cuff stimulation electrode according to claim 10, wherein the control device extracts a heart rate signal from the at least one sensor.

12. The vagus nerve stimulation system according to claim 1, wherein the control device processes posture signals and pressure signals that are generated by the tilt sensor and the pulsation sensor, respectively, and wherein the control device evaluates the pressure signals based on the posture signal, if the posture signal indicates a predetermined change of the orientation of the tilt sensor.

13. The vagus nerve stimulation system according to claim 1, wherein the control device is an implantable pulse generator with an internal power source.

14. The cuff stimulation electrode according to claim 1, wherein the inner cuff surface at least partially surrounds and contacts the nerve.

15. The cuff stimulation electrode according to claim 1, further comprising biocompatible strings attached to the outer wall to enable opening of the cuff stimulation electrode.

* * * * *